United States Patent
Urmey

(10) Patent No.: US 6,533,732 B1
(45) Date of Patent: Mar. 18, 2003

(54) NERVE STIMULATOR NEEDLE GUIDANCE SYSTEM

(76) Inventor: William F. Urmey, 1 Flint Ave., Larchmont, NY (US) 10538

(*) Notice: Subject to any disclaimer, the term of this patent is extended or adjusted under 35 U.S.C. 154(b) by 5 days.

(21) Appl. No.: 09/773,123

(22) Filed: Feb. 1, 2001

Related U.S. Application Data

(60) Provisional application No. 60/241,141, filed on Oct. 17, 2000.

(51) Int. Cl.⁷ ................................................. A61B 5/05
(52) U.S. Cl. .................................................... 600/554
(58) Field of Search ................................. 600/554, 547, 600/507; 604/19, 20, 21, 22, 23, 24, 25, 26, 27, 28; 606/32–52

(56) References Cited

U.S. PATENT DOCUMENTS

| | | | |
|---|---|---|---|
| 3,682,162 A | | 8/1972 | Colyer |
| 4,207,897 A | | 6/1980 | Lloyd |
| 4,515,168 A | | 5/1985 | Chester |
| 4,824,433 A | | 4/1989 | Marz |
| 5,284,153 A | | 2/1994 | Raymond |
| 5,306,236 A | | 4/1994 | Blumenfeld |
| 5,779,642 A | | 7/1998 | Nightengale |
| 5,830,151 A | | 11/1998 | Hadzic |
| 5,853,373 A | | 12/1998 | Griffith |
| 5,885,219 A | | 3/1999 | Nightengale |
| 6,238,371 B1 | * | 5/2001 | Himbert et al. ............. 604/187 |
| 6,298,256 B1 | * | 10/2001 | Meyer ........................ 600/373 |
| 6,325,764 B1 | * | 12/2001 | Griffith et al. .............. 600/554 |

OTHER PUBLICATIONS

Morris, Gary et al., *Innovations in Lower Extremity Blockade*, Techniques in Regional Anesthesia and Pain Management, vol. 3, No. 1, Jan. 1999 pp 9–18.

Chelly, Jacques, et al., *Sciactic Nerve Blocks*, Techniques in Regional Anesthesia and Pain Management, vol. 3, No. 1 Jan. 1999 pp 39–46.

Urmey, William F., *Femoral Nerve Block for the Management of Postoperative Pain*, Techniques in Regional Anesthesia and Pain Management, vol. 1, No. 2 Apr. 1997, pp 88–92.

Urmey, William F., *Upper Extremity Blocks*, Regional Anesthesia and Analgesia, W.B. Saunders Co. 1996 pp 254–278.

Shannon, J. et al. *Lateral Femoral Cutaneous Nerve Block Revisited*, Regional Anesthesia 20(2) 1996 pp 100–104.

* cited by examiner

Primary Examiner—Max F. Hindenburg
Assistant Examiner—Pamela L Wingood
(74) Attorney, Agent, or Firm—Seth Natter; Natter & Natter

(57) ABSTRACT

A target nerve or nerve plexus registration point is percutaneously located using a cutaneous nerve stimulator electrode to elicit response. The electrode includes a tip at the end of a coaxial cylindrical body. A central bore extends through the electrode and carries a nerve stimulator needle. The needle is inserted at the located registration point with the needle path being mechanically guided by the bore, thereby avoiding errant needle passes. A peripheral flange of the body serves as a depth guide in assuring appropriate depression of epidural layers for electrical conductivity and for fixation of the nerve. A nerve stimulator current generator supplies both the percutaneous electrode and the nerve stimulator needle and includes multiple outputs as well as base and variable current setting levels as appropriate for each aspect of the technique and for the specific nerve or nerve plexuses being treated.

26 Claims, 4 Drawing Sheets

NERVE STIMULATOR NEEDLE GUIDANCE SYSTEM

RELATED APPLICATIONS

This application claims the benefit of U.S. Provisional Application No. 60/241,141 filed Oct. 17, 2000.

BACKGROUND OF THE INVENTION

1. Field of the Invention

This invention relates generally to regional anesthesia and more particularly to an apparatus and procedure for nerve stimulator needle guidance in conjunction with various procedures, such as, the administration of an anesthetic blockade, neuro monitoring, electromyography and therapeutic intervention.

2. Antecedents of the Invention

The field of regional anesthesia relates to the practice of administering anesthesia to a specific body region during surgery, for the relief of postoperative pain, and for extended relief of trauma or chronic pain. Often, regional anesthesia has been found to be preferable to general anesthesia because of increased safety, the availability of postoperative pain control and decreased anesthetic costs.

Regional anesthesia delivery techniques strove to optimize administration of a local anesthetic in close proximity to a target or nerve plexus so as to establish a neural blockade. Successful administration of regional anesthesia was dependent upon the accurate placement of the anesthetic in relation to the target nerve or nerves.

Various techniques have been employed to assist in placement of an administration needle in close proximity to the target nerve which was not externally visible. One of the traditional methods of needle placement involved eliciting paresthesia. Among the disadvantages of this technique was the lack of accurate patient responses amongst patients who were disoriented and/or sedated.

A prevalent technique employed the use of nerve stimulators electrically coupled to a nerve stimulator needle. Such method was premised upon the phenomenon that an electrical pulse is capable of stimulating a motor nerve fiber to contract an innervated muscle or cause paraesthesia, in the case of sensory nerve stimulation.

Nerve stimulators generally comprised a power supply, a pulse generating circuit and current adjusting means, e.g. the DIGISTIM III nerve stimulator sold by Neuro Technology Inc. of Houston, Tex., coupled to insulated or uninsulated anesthesia needles. U.S. Pat. No. 4,515,168, issued to CHESTER illustrates a nerve stimulator which mounts directly upon a syringe and needle.

Suggested improvements in techniques of utilizing nerve stimulator needles have been exemplified by the patents to GRIFFITH (U.S. Pat. No. 5,853,373), HADZIC (U.S. Pat. No. 5,830,151), RAYMOND (U.S. Pat. No. 5,248,153) and CHESTER (U.S. Pat. No. 4,515,168), which were directed to avoiding the requirement for the presence of an assistant in order to reduce the current levels as the needle was advanced toward the target nerve or nerve plexus.

The nerve stimulator needle, e.g. a CONTIPLEX nerve block set sold by B. Braun Medical, Inc. of Bethlehem, Pa., was placed within the tissue of the patient's body in the vicinity of the nerve to be blocked and then advanced until stimulation of the target nerve was achieved as determined by visually detecting muscle contractions or by eliciting a report that the patient felt the stimulus in response to the current flow through the stimulator needle.

The current supplied by the nerve stimulator was reduced as the nerve stimulator needle was further advanced, until stimulation of the target nerve was achieved using a reduced current level associated with a prescribed distance between the needle tip and the target nerve.

Thereafter, a portion of the anesthetic dose was administered through the needle to terminate the response to the nerve stimulation current. If the response was terminated by the initial administration, the needle was deemed to be properly positioned in proximity to the target nerve and the remaining dose of anesthetic was administered.

It should be understood, however, that the initial placement of the needle was dependent upon anatomic landmarks. Since anatomic landmarks varied from patient to patient, they constituted only an approximate starting zone or region to guide needle insertion. Successful administration was often dependent upon the skill and experience of the anesthesiologist. Multiple needle passes were required when the initial needle placement was not directly registered over the target nerve or nerve plexus or when the angle of introduction was anatomically incorrect.

Peripheral nerves have been stimulated with cutaneous electrodes at appropriate landmarks utilizing a coupling gel for monitoring the degree of neuromuscular blockade during general anesthesia when neuromuscular relaxing or paralyzing drugs were intravenously administered.

BRIEF SUMMARY OF THE INVENTION

A nerve stimulator needle guidance system includes a cutaneous electrode having a conductive tip at the end of a cylindrical body with a bore extending coaxially through the body and tip.

The cutaneous electrode is coupled to a nerve stimulator to locate a target nerve registration point while depressing the patient's dermal layers. Thereafter a nerve stimulator needle, coupled to the nerve stimulator, is introduced into the patient at the located registration point through the bore. Conventional nerve stimulation techniques are employed to properly position the needle tip adjacent to the target nerve for the administration of anesthesia or other treatment.

The cutaneous electrode bore serves as a guide for the initial placement of the needle at the registration point and for guidance of the needle travel path toward the target nerve. Maintaining the dermal layers in a depressed or indented state by continued pressure on the cutaneous electrode serves to fix the location of the target nerve.

From the foregoing compendium, it will be appreciated that it is an aspect of the present invention to provide a nerve stimulator needle guidance system of the general character described which is not subject to the disadvantages of the antecedents of the invention.

It is a feature of the present invention to provide a nerve stimulator needle guidance system of the general character described which simplifies the administration of nerve blockade anesthesia.

A consideration of the present invention to provide a nerve stimulator needle guidance system of the general character described which increases the likelihood of the successful administration of regional anesthesia with a single needle pass.

A feature of the present invention is to provide a nerve stimulator needle guidance system of the general character described which noninvasively locates the entry point of a nerve stimulator needle.

To provide a nerve stimulator needle guidance system of the general character described which is well suited for conventional sterilization techniques is a further consideration of the present invention.

An aspect of the present invention is to provide a nerve stimulator needle guidance system of the general character described which decreases the likelihood of anesthesia administration complications resulting from errant needle passes.

An additional consideration of the present invention is to provide a nerve stimulator needle guidance system of the general character described with increased nerve block success levels.

A further feature of the present invention is to provide a nerve stimulator needle guidance system of the general character described with reduced patient discomfort attributable to multiple needle passes.

To provide a nerve stimulator needle guidance system of the general character described with increased safety is a further aspect of the present invention.

Yet a further consideration of the present invention is to provide a nerve stimulator needle guidance system of the general character described which minimizes the time required to achieve a nerve blockade.

To provide a nerve stimulator needle guidance system of the general character described which is simple to use is a further aspect of the present invention.

A still further aspect of the present invention is to provide a nerve stimulator needle guidance system of the general character described which is economically disposable after a single usage.

Another feature of the present invention is to provide a nerve stimulator needle guidance system of the general character described which lends itself to economical mass production fabrication.

Other aspects, features and considerations of the present invention in part will be obvious and in part will be pointed out hereinafter.

With these ends in view, the invention finds embodiment in certain combinations of elements, arrangements of parts and series of steps by which the said aspects, features and considerations and certain other aspects, features and considerations are attained, all with reference to the accompanying drawings and the scope of which will be more particularly pointed out and indicated in the appended claims.

BRIEF DESCRIPTION OF THE DRAWINGS

In the accompanying drawings in which are shown some of the various possible exemplary embodiments of the invention.

DESCRIPTION OF THE PREFERRED EMBODIMENTS

Figure 1:
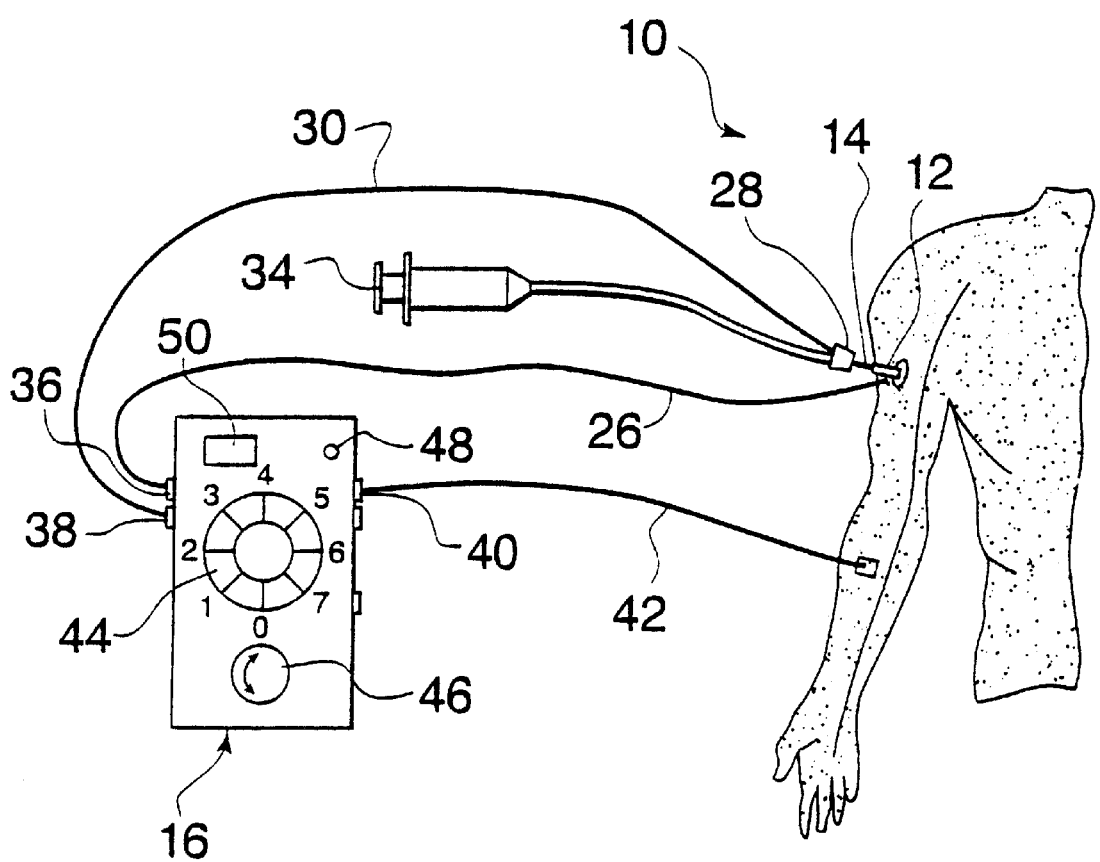
FIG. 1 is a schematized illustration of a nerve stimulator needle guidance system constructed in accordance with and embodying the invention being employed to locate a target median nerve of a patient and illustrating a cutaneous electrode, a nerve stimulator needle positioned within the bore of the cutaneous electrode and with both being coupled to a nerve stimulator.
Figure 2:
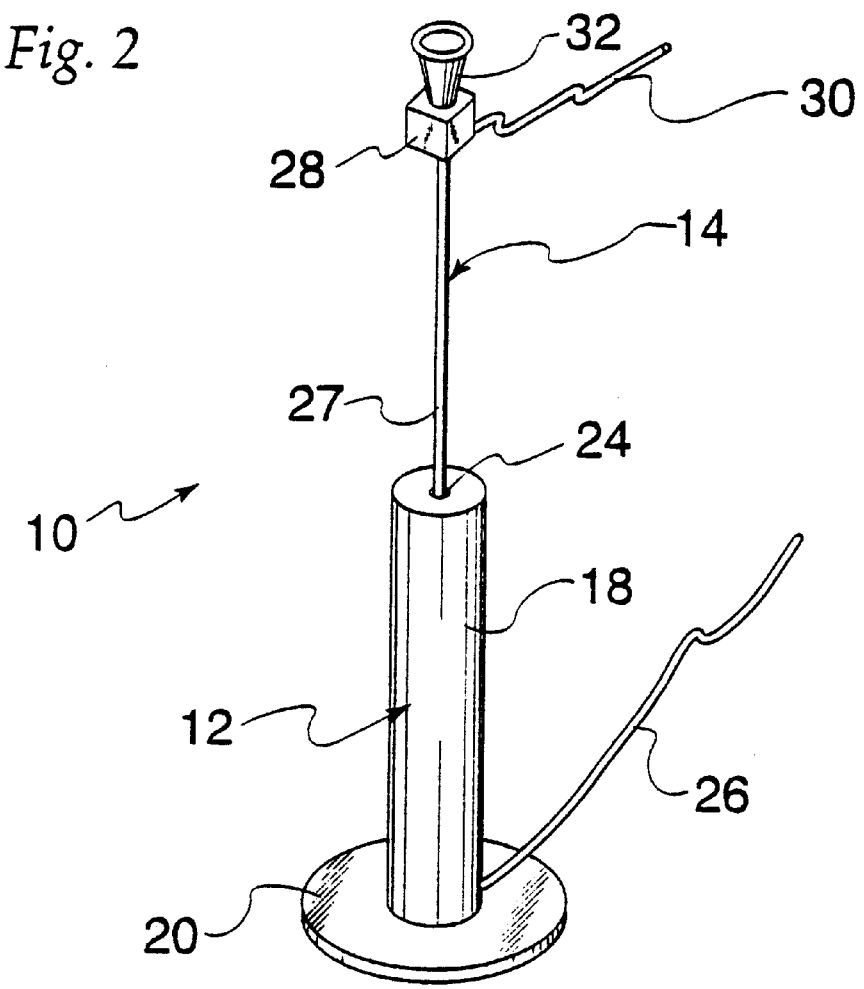
FIG. 2 is a perspective illustration of the nerve stimulator needle guidance system and showing a cylindrical body and a flange of the cutaneous electrode as well as a nerve stimulator needle positioned within the bore of the cutaneous electrode.
Figure 3:
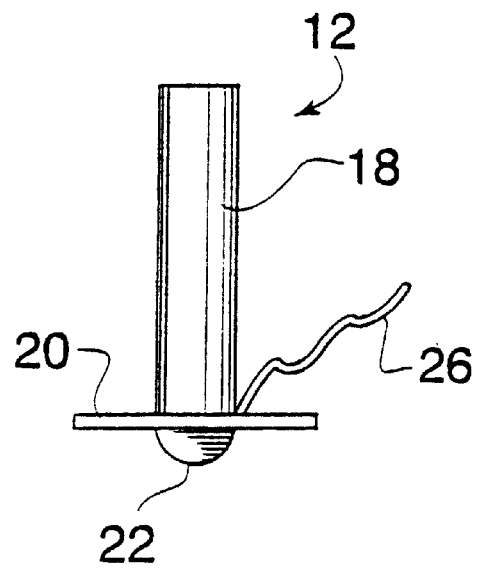
FIG. 3 is a front elevational view of the cutaneous electrode and illustrated a hemispherical conductive tip of the electrode positioned beneath the peripheral flange.

With reference now in detail to the drawings, wherein like numerals denote like components throughout the various figures, the reference numeral 10 denotes generally a nerve stimulator needle guidance system constructed in accordance with and embodying the invention. The system includes a cutaneous electrode 12 which is employed to locate a target nerve registration point on a patient's skin and a nerve stimulator needle electrode 14 which is introduced into the patient at the located registration point with both electrodes being coupled to a nerve stimulator 16.

It should be noted that the cutaneous electrode 12 generally comprises a non-conductive body 18, depicted in the figures as having a cylindrical shape, in an exemplary configuration. A transverse flange 20 projects laterally from the lower end of the body 18 and a generally hemispherical electrically conductive tip 22 is positioned below the flange 20 and in registration with the body 18. A bore 24 extends coaxially through both the body and the conductive tip and an electrical lead 26 couples the conductive tip to the nerve stimulator 16.

The nerve stimulator needle 14 is of generally conventional configuration and includes a needle shaft 27 which may be coated with a nonconductive material, except for the tip portion thereof. At the proximal end of the shaft 27 is a connector block 28 from which an electrical lead 30 extends to electrically couple the nerve stimulator needle 14 to the nerve stimulator 16. A conventional Luer fitting 32 may be mounted to the connector block to couple the needle bore to a conventional syringe 34.

With reference to FIG. 1, the nerve stimulator 16 includes known pulse generating and adjustable current control circuits such as those employed in the DIGISTIM III, supra or those disclosed in U.S. Pat. No. 4,515,168, incorporated herein by reference. Multiple base current setting levels and outputs are provided, however. One output terminal 36 is provided for the cutaneous electrode 12 and another output terminal 38 is provided for the nerve stimulator needle 14, with the respective electrical leads 26, 30 being coupled to their associated terminals.

The nerve stimulator 16 also includes a ground terminal 40 to which is coupled a ground output lead 42, the end of which is electrically coupled to the patient in a conventional manner.

A base level output current setting control 44 is operable to adjust to the optimal initial or base level currents and current ratios through the terminals 36, 38 suitable for employment in conjunction with a specified target nerve or nerve plexus.

For each of the various target nerves, e.g. femoral nerve, popliteal fossa approach to sciatic nerve, mid-humeral approach to median nerve, ulnar nerve, sciatic nerve, interscalene brachial plexus approach to C5 and C6 nerve roots, etc., optimal initial or base level current flow through the cutaneous electrode terminal 36 and the stimulator needle terminal 38 are provided.

The cutaneous electrode current flow may be within an overall range of 2–10 mA, for example, and nerve stimulator needle current flow may be within an overall range of 0.3–3.0 mA, for example. By way of further example, minimum cutaneous electrical current for location of the femoral nerve may be achieved at 5 mA while the minimum stimulator needle current flow may be at 0.5 mA.

The nerve stimulator 16 also includes a variable current adjustment control 46 and an output selector switch 48 for selecting either the cutaneous electrode terminal 36 or the nerve stimulator needle terminal 38. Also provided is a display 50 for quantitatively indicating current flow through the active terminal or other data.

It should be understood that the nerve stimulator needle guidance system 10 may be utilized with a conventional nerve stimulator having, for example, a single output and with operating room personnel disconnecting the cutaneous electrode lead 26 and connecting the nerve stimulator needle lead 30 after the target point has been cutaneously located. It should be appreciated that the output will simultaneously be adjusted to a reduced level upon introduction of the nerve stimulator needle into the patient.

It is also possible to practice the invention utilizing two separate nerve stimulators, one coupled to the cutaneous electrode and the other coupled to the nerve stimulator needle.

Figure 4:
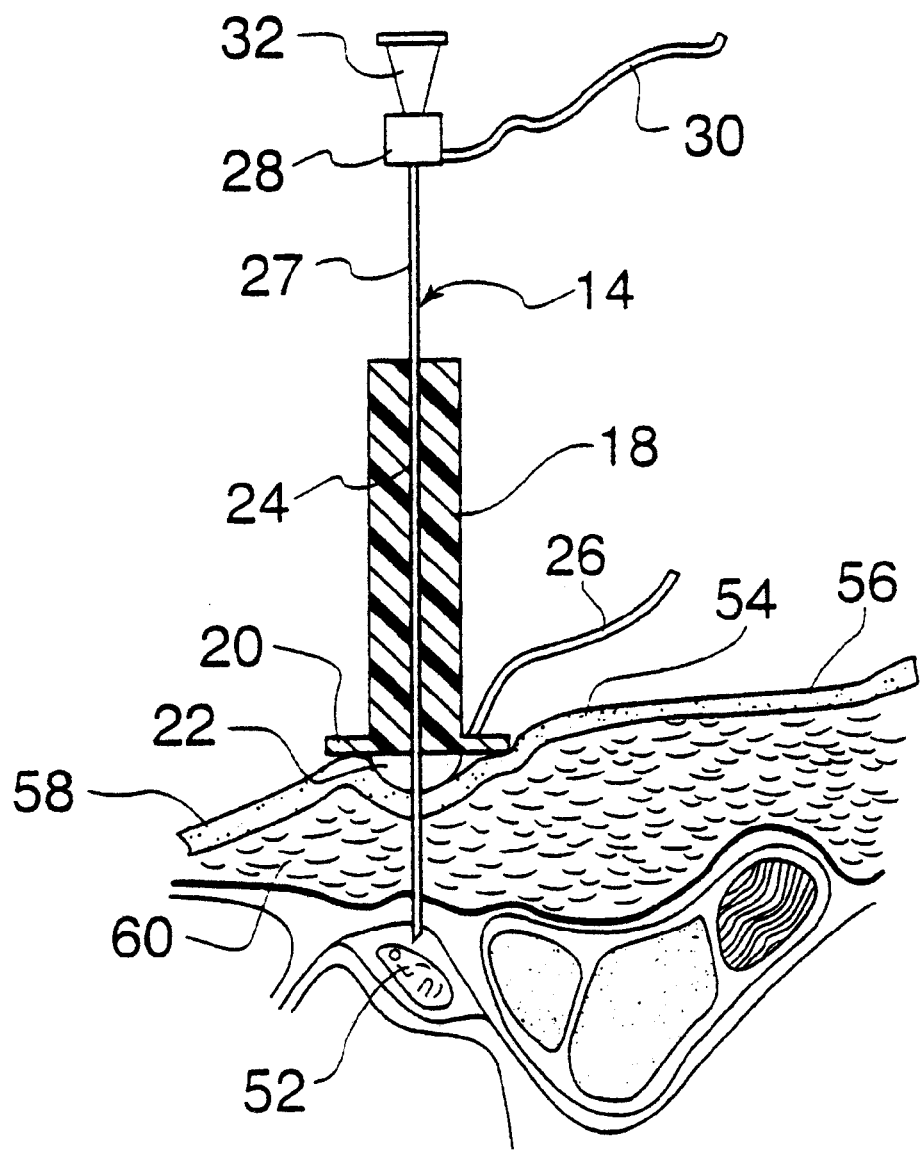
FIG. 4 is a sectional view through the nerve stimulator needle guidance system and illustrating the technique of employing the nerve stimulator needle guidance system for the purpose of locating a femoral nerve for inguinal perivascular femoral nerve block techniques.

FIG. 4 illustrates, in an exemplary manner, the implementation of the present invention in the administration of a nerve block to a patient's femoral nerve 52. Initially, as under conventional practice, the patient receives prescribed amounts of intravenous sedatives in accordance with conventional routines for nerve location utilizing nerve stimulators.

A sterile coupling gel 54 may be applied over the patient's skin 56 in the appropriate anatomic region prelocated by landmarks. Thereafter, the cutaneous electrode 18, coupled to the nerve stimulator 16 (illustrated only in FIG. 1) through the lead 26, is forced against the skin 56 and underlying dermis 58, compressing subcutaneous fat 60 such that the flange 20 is essentially flush with the skin. In this regard, the flange 20 may be fabricated of a transparent thermoplastic for ease in assuring that the proper tissue depression by the conductive tip 22 has been achieved.

The nerve stimulator output, with an initial or base current level set by the control 44 illustrated only in FIG. 1, is moved across the skin to noninvasively elicit responses. By reducing current flow at the control 46, illustrated only in FIG. 1 the cutaneous electrode 18 locates a point on the skin 56 which is in registration with the target femoral nerve 52. The registration point is found when it is determined that the appropriate muscle contractions have been elicited with minimum current, that is, maximal motor contractions have been encountered at a minimum current level.

The position of the cutaneous electrode is held fast, i.e., is not moved laterally nor is the compressive force released and current flow through the cutaneous electrode is terminated. The shaft 27 of the nerve stimulator needle 14 is then urged through the bore 24 and into the patient while being electrically coupled through the electrical lead 30 to the appropriate output terminal 38 of the nerve stimulator 16 illustrated in FIG. 1.

Utilizing conventional nerve stimulator techniques, the needle 14 is advanced while current flow reduced through adjustment at the control 46 until stimulation of the femoral nerve is achieved utilizing a reduced current level associated with the prescribed distance between the tip of the needle shaft 27 and the target femoral nerve 52. Maintenance of the compressive force on the cutaneous electrode 18 serves to fix the position of the target nerve while the needle is being advanced.

Thereafter, a portion of the anesthetic dose is administered through the needle to terminate response to the stimulation current. If the response terminates with the initial administration, the needle is deemed to be properly positioned for the requisite procedure.

Figure 5:
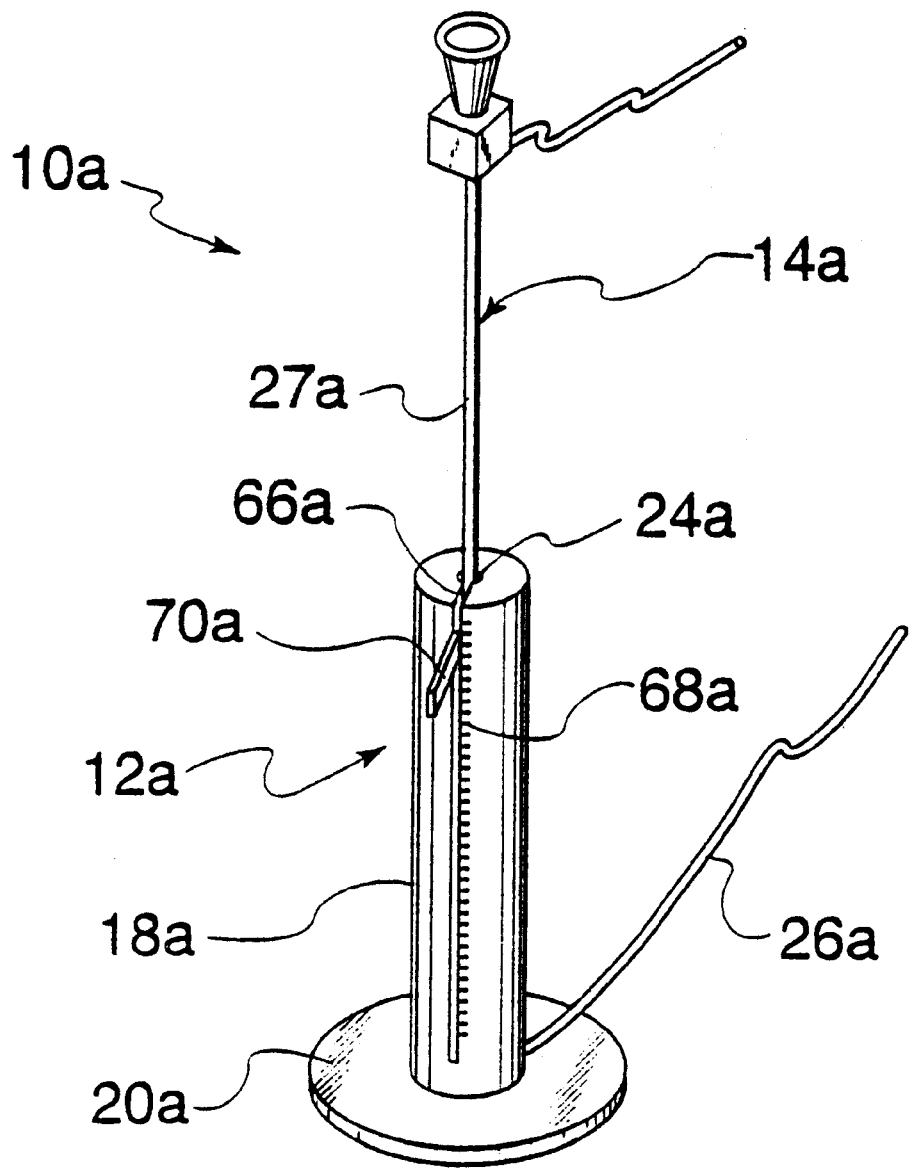
FIG. 5 is a perspective illustration of a further embodiment of the invention wherein the cylindrical body of the cutaneous electrode includes a radial slot and a peripheral indexing scale and with a shaft of the stimulator needle including a radial arm positioned within the slot.

With reference now to FIG. 5, wherein an alternate embodiment of the invention is illustrated, it will be noted that like numerals have been employed to denote like components of the previous embodiment, however, bearing the suffix "a". In the FIG. 5 embodiment, a nerve stimulator needle guidance system 10a includes a cutaneous electrode 12a and a nerve stimulator needle 14a coupled to a nerve stimulator.

The cutaneous electrode 12a includes a nonconductive body 18a, illustrated of generally cylindrical configuration, by way of example only and a lower flange 20a. An electrical lead 26a couples a conductive tip, positioned beneath the flange 20a, to the nerve stimulator. In a manner similar to that with respect to the previous embodiment, the cutaneous electrode 12a includes a bore 24a extending coaxially through a body 18a.

A planar radial slot 66a extends substantially along the entire axial length of the body 18a from the upper end thereof and a plurality of indexing marks 68a appear as a scale along the length of the body adjacent the slot 66a.

A radial indexing arm 70a is fixed to a shaft 27a of the needle 14a and may be employed, in conjunction with the marks 68a, to gauge the depth of penetration of the tip of the needle shaft 27a.

The radial arm 70a may be of sufficient rigidity to be employed for the purpose of advancing the needle shaft 27a into the patient with the anesthesiologist applying a downward force to a portion of the arm 70a which projects radially from the slot 66a.

The technique of employing the nerve stimulator needle guidance system 10a of the alternate embodiment is substantially identical to that employed in conjunction with the previous embodiment, with the exception, however, of enabling the anesthesiologist to utilize the indexing marks as a depth of penetration gauge and also the utilization of the arm 70a for the purpose of advancing the needle shaft into the patient.

It should be appreciated that the nerve stimulator needle guidance system of the present invention may be implemented not only for administering an anesthesia blockade but for other medical techniques and practices wherein nerves or a nerve plexus is to be located for treatment such as electromyography, neuro monitoring and therapeutic intervention.

Thus it will be seen that there is provided a nerve stimulator needle guidance system which achieves the various aspects, features and considerations of the present invention and which is well adapted to meet the conditions of practical usage.

As various possible further embodiments might be made of the present invention and various changes might be made in the illustrative embodiments above set forth, without departing from the spirit of the invention, it is to be understood that all matter herein described or shown in the accompanying drawings is to be interpreted as illustrative and not in a limiting sense.

Having thus described the invention there is claimed as new and desired to be secured by Letters Patent:

1. A nerve stimulator needle guidance system comprising a cutaneous electrode, the cutaneous electrode including an electrically conductive tip, the tip having a smooth surface for traversing over the surface of a patient's skin while maintaining electrical current flow through the patient to locate a cutaneous registration point in proximity with a target nerve or nerve plexus, the smooth surface being incapable of penetrating the patient's skin when forced thereagainst to compress subcutaneous tissue or fat, the tip further including a bore, whereby the located cutaneous registration point may be accessed through the bore by a needle without removing the cutaneous electrode.

2. A nerve stimulator needle guidance system as constructed in accordance with claim 1, the cutaneous electrode further including a body, the tip being positioned at an end of the body, the bore extending coaxially through the body and the tip whereby the located cutaneous registration point may be accessed through the body.

3. A nerve stimulator needle guidance system as constructed in accordance with claim 2 further including a flange, the flange extending laterally from the body and being positioned on the body adjacent the tip.

4. A nerve stimulator needle guidance system as constructed in accordance with claim 1 further including a nerve stimulator needle, the needle being positioned in the bore for translational movement through the patient's skin at the registration point.

5. A nerve stimulator needle guidance system as constructed in accordance with claim 4 wherein the needle includes a shaft, the shaft having a distal end, the exterior surface of the distal end of the shaft being electrically conductive, the exterior surface of the remainder of the shaft being electrically nonconductive.

6. A nerve stimulator needle guidance system as constructed in accordance with claim 1 wherein the smooth surface is curved.

7. A nerve stimulator needle guidance system as constructed in accordance with claim 6 wherein the tip is hemispherical in shape.

8. A method of positioning a needle for physiological administration at an internal anatomic target, the method including the steps of:
   a) moving a smooth surface member having a needle guide along a cutaneous surface until a point in registration with the target is located,
   b) inserting a tip of the needle through the cutaneous surface at the located point, and
   c) utilizing the needle guide to direct a path of needle travel toward the target while maintaining the smooth surface member at the located point.

9. A method of positioning a needle for physiological administration in accordance with claim 8 wherein step b) is practiced by utilizing the needle guide to position the needle tip for insertion.

10. A method of positioning a needle for physiological administration in accordance with claim 8 wherein smooth surface member comprises an electrode and the point is located utilizing a nerve stimulator coupled to the smooth surface member.

11. A method of positioning a needle for physiological administration in accordance with claim 8 wherein the needle is a nerve stimulator needle and the target comprises a nerve or nerve plexus, the method further including the step of:
   d) employing a nerve stimulator coupled to the nerve stimulator needle to position the tip of the needle in proximity to the nerve or nerve plexus.

12. A method of positioning a needle for physiological administration in accordance with claim 8 wherein the smooth surface member is pressed against the cutaneous surface in step a) and pressure is maintained during step b) and step c).

13. A needle guidance system suitable for locating a target nerve or a nerve plexus in a subject, the system comprising a guiding electrode, the guiding electrode having a smooth tip, the guiding electrode being selectively coupled to a current supply for eliciting a neurological response to current flow through the subject, the guiding electrode including a bore, a needle carried in the bore, the needle being movable within the bore relative to the guiding electrode the needle selectively coupled to a current supply for eliciting a neurological response to current flow through the subject when the needle is advanced into the subject through the bore and toward the target nerve or nerve plexus.

14. A needle guidance system as constructed in accordance with claim 13 wherein the guiding electrode includes a body and a conductive tip, the system further including an electrical lead for coupling the conductive tip to the current supply.

15. A needle guidance system as constructed in accordance with claim 13 wherein the guiding electrode current supply comprises a nerve stimulator.

16. A needle guidance system as constructed in accordance with claim 13 wherein the needle current supply comprises a nerve stimulator.

17. A needle guidance system as constructed in accordance with claim 13 wherein the guiding electrode current supply and the needle current supply comprise a nerve stimulator having an output for coupling to the guiding electrode and a further output for coupling to the needle.

18. A needle guidance system as constructed in accordance with claim 13 wherein the guiding electrode includes an axial slot extending from the bore and the needle includes a radial arm fixed to the needle, the radial arm being received in the slot.

19. A needle guidance system as constructed in accordance with claim 18 wherein the guiding electrode further includes indicia adjacent the slot, whereby the depth of penetration of the needle may be gauged.

20. A method of locating a target nerve or nerve plexus for the administration of an anesthetic blockade or other treatment regimen, the method comprising the steps of:
   a) locating a point in registration with the target nerve or nerve plexus utilizing a guiding electrode coupled to a nerve stimulator,
   b) utilizing the guiding electrode to advance a nerve stimulator needle coupled to a nerve stimulator into the patient at the located point,
   c) extending the needle beyond the point toward the target nerve or nerve plexus, and
   d) detecting when the nerve stimulator needle is properly positioned by observing when the maximal neural response is attained at the minimum current level.

21. A method of locating a target nerve or nerve plexus for the administration of an anesthetic blockade or other treatment regimen in accordance with claim 20 wherein the step of locating includes applying a compressive force through the guiding electrode and the step of utilizing the guiding electrode to advance the nerve stimulator needle is practiced while maintaining the compressive force, whereby the target nerve or nerve plexus is fixed in position while the nerve stimulator needle is advanced.

22. A method of locating a target nerve or nerve plexus in accordance with claim 21 wherein the guiding electrode includes a bore, and the point is located on a cutaneous surface.

23. A method of locating a target nerve or nerve plexus for the administration of an anesthetic blockade or other treatment regimen in accordance with claim 21 wherein the guiding electrode includes a bore and the step of utilizing the guiding electrode to advance the nerve stimulator needle includes advancing the nerve stimulator needle through the bore.

24. A method of locating a target nerve or nerve plexus for the administration of an anesthetic blockade or other treatment regimen in accordance with claim 23 wherein the nerve stimulator needle is guided during step b) and step c) by the bore.

25. A method of locating a target nerve or nerve plexus for the administration of an anesthetic blockade or other treatment regimen in accordance with claim 20 wherein the guiding electrode is maintained in a fixed position during step b) and step c).

26. A method of locating a target nerve or nerve plexus for the administration of an anesthetic blockade or other treatment regimen in accordance with claim 20 further including the step of controlling the nerve stimulator to provide current flow only through the electrode during step a) and to provide current flow only through the needle during step c).

* * * * *